United States Patent [19]

Jacobs et al.

[11] Patent Number: 5,759,010

[45] Date of Patent: Jun. 2, 1998

[54] SEALED CARTRIDGE TO IMPROVE CHEMISTRY STABILITY OF TEST ELEMENTS

[76] Inventors: Merrit Nyles Jacobs; Gary Francis Gnolek; Dale Bruce Nash; Gerald George Meiler; Johannes Jacobus Porte, all of Johnson & Johnson Clinical Diagnostics, Inc., Rochester, N.Y. 14650-0880

[21] Appl. No.: 598,757

[22] Filed: Feb. 8, 1996

Related U.S. Application Data

[60] Provisional application No. 60/007,249, Nov. 6, 1995.
[51] Int. Cl.⁶ ............................................. B65G 59/02
[52] U.S. Cl. ........................ 414/796.8; 414/786; 422/104
[58] Field of Search ........................ 414/796.8; 422/63, 422/102, 104

[56] References Cited

U.S. PATENT DOCUMENTS

| | | | |
|---|---|---|---|
| 4,190,420 | 2/1980 | Covington et al. | 422/63 |
| 4,512,952 | 4/1985 | Blanding et al. | 414/796.8 X |
| 4,814,279 | 3/1989 | Sugaya | 435/289 |
| 5,043,143 | 8/1991 | Shaw et al. | 422/104 X |
| 5,330,716 | 7/1994 | Shaw et al. | 422/63 |
| 5,599,505 | 2/1997 | Fujisaki et al. | 422/104 |

*Primary Examiner*—Janice L. Krizek
*Attorney, Agent, or Firm*—Dana M. Schmidt

[57] ABSTRACT

An improved cartridge and method of dispensing test elements therefrom, which seals off the elements from exposure to the atmosphere. The cartridge includes, at its end apertured to eject test elements, a cover plate, said plate optionally being biased into contact with the end-most test element to cover the fluid opening provided in all such test elements. To dispense that end-most element, a pusher blade engages and ejects the element as in conventional cartridges. Optionally, the opposite end of the cartridge is sealed with a duck-bill seal.

8 Claims, 4 Drawing Sheets

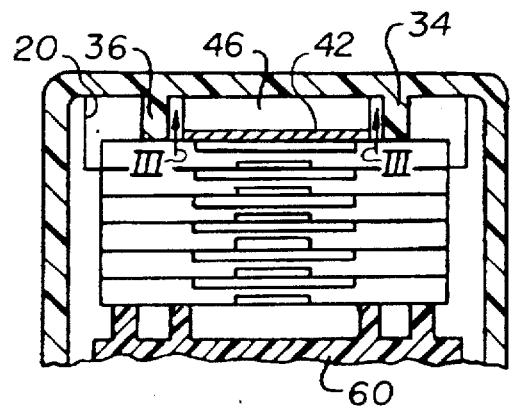
FIG. 2
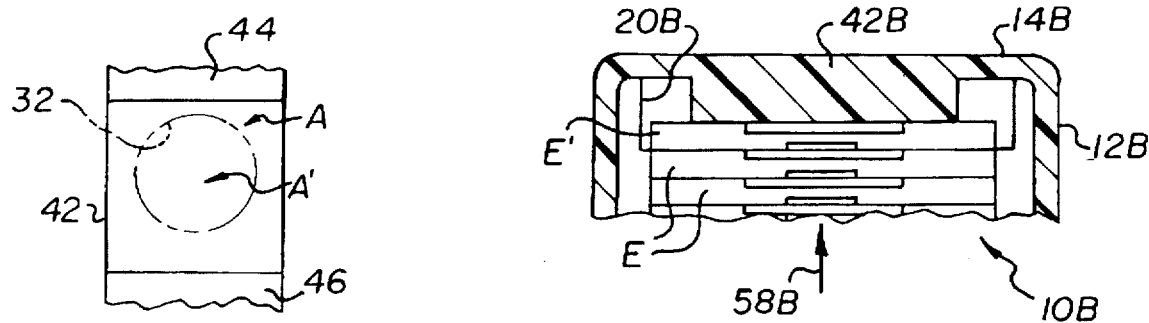
FIG. 3
FIG. 7
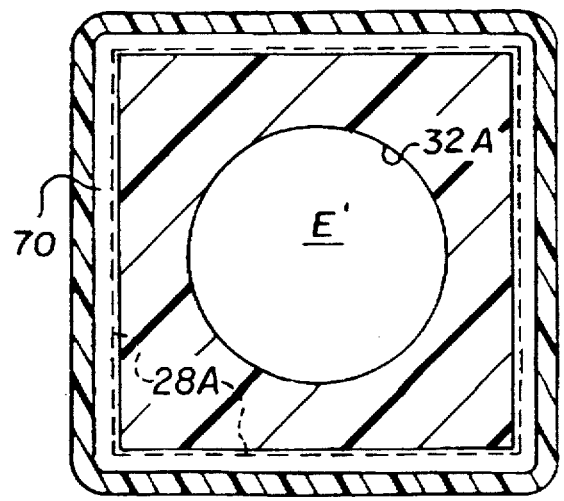
FIG. 5

# 5,759,010

SEALED CARTRIDGE TO IMPROVE CHEMISTRY STABILITY OF TEST ELEMENTS

CROSS-REFERENCE TO RELATED APPLICATION

This application claims the benefit of U.S. Provisional application Ser. No. 60/007,249, field on Nov. 6, 1995, entitled, Sealed Cartridge To Improve Chemistry Stability Of Test Elements.

FIELD OF THE INVENTION

This invention relates to cartridges for storing test elements prior to use with patient sample to detect clinical analytes, and especially to a temporary seal internal of the cartridge to protect the test elements from exposure to the atmosphere during storage.

BACKGROUND OF THE INVENTION

It has been conventional practice to supply stacks of slide test elements to clinical analyzers, stored in cartridges. These cartridges comprise a housing with opposing ends and the stack between them, a first end being apertured to allow a pusher blade to enter and eject the test element of the stack (e.g., the top-most element) from the cartridge. See, e.g., U.S. Pat. No. 4,190,420.

Although such cartridges have functioned well, as is evidenced by sales of over 1 billion test elements for "Ektachem"® brand analyzers, there remains a minor problem: Said apertures for blade entry and test element ejection allow exposure of the test elements within, to the atmosphere. (The test elements each have a liquid access opening that exposes the chemistry.) This is particularly the case for the test element closest to the dispensing end. That effect is called the "first slide effect", and is a bias in performance, possibly due to oxidizing caused by the air exposure. In addition, lesser biases can be found in test elements covered by the first element, since there is no seal between the cartridge sidewalls and the remainder of the stack, and no complete seal between test elements. However, because remaining test elements are contacted and covered by the previous test element, less air from any source can enter the liquid access opening of the remaining test elements —hence, the bias in the test elements covered by the first element is reduced.

Obvious solutions would be of course to tape over the entry and ejecting apertures with a hermetically sealing foil that is removed when dispensing is needed. However, this has not been satisfactory because such a foil has to be removed either a) by hand or b) by the analyzer. Such removal is not trivial, given the cost of labor and robotic removers. Additionally, such a foil does not solve the exposure problem once the first test element is dispensed. Because the cartridge may THEN be stored without use, the next test element in the stack suffers the "first slide effect" until it is dispensed. If storage between ejections of test elements is short, there is little problem. However, the usage of the analyzer can never guarantee that the storage will be short.

Finally, it has been discovered recently that a total hermetic seal of a wrapping around the cartridge is insufficient protection during keeping, whether or not under frozen conditions, for reasons that are not understood. That is, the top-most test element appears to be exposed to whatever is sealed within the wrapping, to its detriment.

Thus, it has been a long-standing problem, prior to this invention, that test elements stored in stacks in such cartridges have experienced a drift or bias in performance that is most pronounced the closer the test element comes to being the stored "first slide", such drift or bias not being totally preventable by a total hermetic wrap.

SUMMARY OF THE INVENTION

We have produced a cartridge design and method of use that overcome the afore-noted problems.

More specifically, in accord with one aspect of the invention, there is provided a cartridge of slide test elements stacked one upon the other and each having an opening for liquid access, the cartridge comprising a first dispensing end; a second, opposing end, the first end including an aperture for the ejection of a slide test element closest to the first end. The cartridge is improved in that the cartridge further includes, adjacent to the first end and the aperture, an impervious cover plate mounted in sealing contact with said closest test element, said cover plate having a surface area that is greater in extent than the surface area of said opening, so that the cover plate removably seals off atmospheric exposure of the opening of the closest test element.

In accord with another aspect of the invention, there is provided a method of storing and ejecting slide test elements in a stack contained in a cartridge having an aperture at a first end of the stack that otherwise exposes the stack to the atmosphere, the test elements comprising a frame having a liquid access opening allowing liquid to flow into the test element, the method comprising the steps of releasibly covering the access opening of the test element closest to the aperture, the access openings of remaining test elements of the stack being in covered contact with a test element closer to the aperture than the remaining element, and when a test element is needed, uncovering the access opening of the closest test element while simultaneously pushing a pusher blade into one of the apertures into contact with the test element closest to the aperture to eject the closest test element from the stack.

Accordingly, it is an advantageous feature of the invention that "first slide effect" biases are reduced or eliminated, whether the test element in question is, in fact, the very first in the stack as shipped from the manufacturer, or becomes the "first" due to storage following the dispensing of previous test elements.

Other advantageous features will become apparent upon reference to the following Detailed Description, when read in light of the attached drawings.

BRIEF DESCRIPTION OF THE DRAWINGS

FIG. 2 is a section view taken generally along the line II—II of FIG. 1;

FIG. 3 is a fragmentary bottom view taken generally along the line III—III of FIG. 2;

FIG. 5 is a section view taken generally along the line V—V of FIG. 4;

FIG. 7 is a view similar to that of FIG. 2, but of yet another embodiment.

DESCRIPTION OF THE PREFERRED EMBODIMENTS

The following description concerns the preferred embodiments, wherein there is described a particular cartridge configuration for a stack of preferred test elements, dispensed from the top of the cartridge. In addition, the invention is useful regardless of the cartridge configuration, or the particular slide test elements of the stack, and regardless whether the test elements are dispensed from the top, or bottom of the stack.

Figure 1:
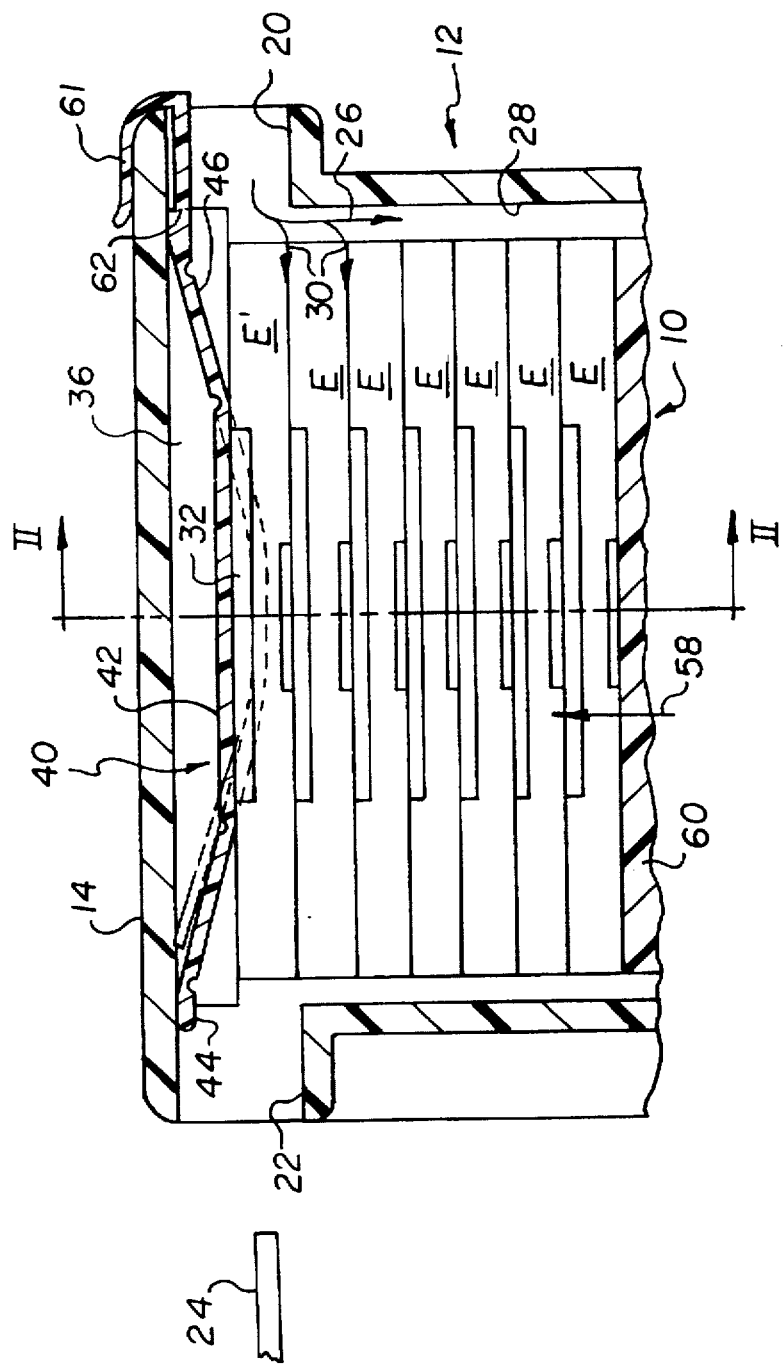
FIG. 1 is a fragmentary vertical elevation view in section of a cartridge constructed in accord with the invention.

Referring to FIG. 1, the invention is preferably used to store a stack 10 of slide test elements E and E' such as those available under the trademark "Ektachem"® from Johnson & Johnson Clinical Diagnostics, Inc. Such a stack is preferably contained during storage within a cartridge 12 constructed as taught by U.S. Pat. No. 4,190,420. More specifically, a top end 14 of the cartridge has at least one aperture 20 for the ejection of a test element E, and an opposing aperture 22 for the entrance of a pusher blade 24 that engages the top-most test element in the stack. It is these apertures that constitute a first level of exposure of the contained stack, to the degrading influences of the atmosphere. However, we have found that, even when the apertures 20 and 22 are sealed, as by a bag completely and hermetically enclosing the cartridge, there is a second level of exposure because of the gap represented by arrow 26, between the stack 10 and the inside wall surface 28 of cartridge 12. Flow also passes, arrows 30, between the members of the stack, to a slight degree. In any event, openings 32 in the top of the test elements E, as is well-known, are liquid access openings which perforce expose the test elements to the atmosphere within the cartridge, at least.

Guide rails 34.36 are provided, FIG. 2, for various functions of the cartridge, as explained in the aforesaid '420 patent. The top-most test element E' is preferably pushed up, arrow 58, until it contacts the rails, as shown.

In accordance with one aspect of the invention, a seal over the opening 32 of the top-most test element E', is provided by an element 40 comprising at least a cover plate 42 having a surface area A, FIG. 3, that is larger than the surface area A' of the access opening 32 of the test element underneath it (shown in phantom). Optionally and preferably, it also includes at least a biasing member, preferably two in the form of leaf spring legs 44,46, extending upwardly away from plate 42. Legs 44,46 position cover plate 42 so that it completely -covers area A', and thereby seals off opening 32 of the test element it contacts.

Most preferably, leg 46 includes a clip portion 61 that secures leg 46 to top end 14 of the cartridge, to keep plate 42 centered. Alternatively, clip portion 61 can be removed at 62, so both legs are free to slip, as shown in phantom for leg 44.

It will be readily appreciated that cover plate 42 need not be permanently flat, as shown in solid lines. Rather, in the absence of test elements E pressing upwardly, it can be bowed as shown in phantom, inasmuch as such becomes flattened when elements E,E' are inserted and pressed upwardly, arrow 58, by anti-back-up member 60.

When used, the top-most test element E' is engaged by blade 24 and ejected off stack 10 and out aperture 20. Anti-backup member 60 keeps the stack pushed upward, as is taught in the '420 patent.

A further alternative is that the spring element can comprise a compressed coil spring instead of a leaf spring (not shown), pushing down on the cover plate. It will be readily apparent that more than one compression spring can be used.

Figure 4:
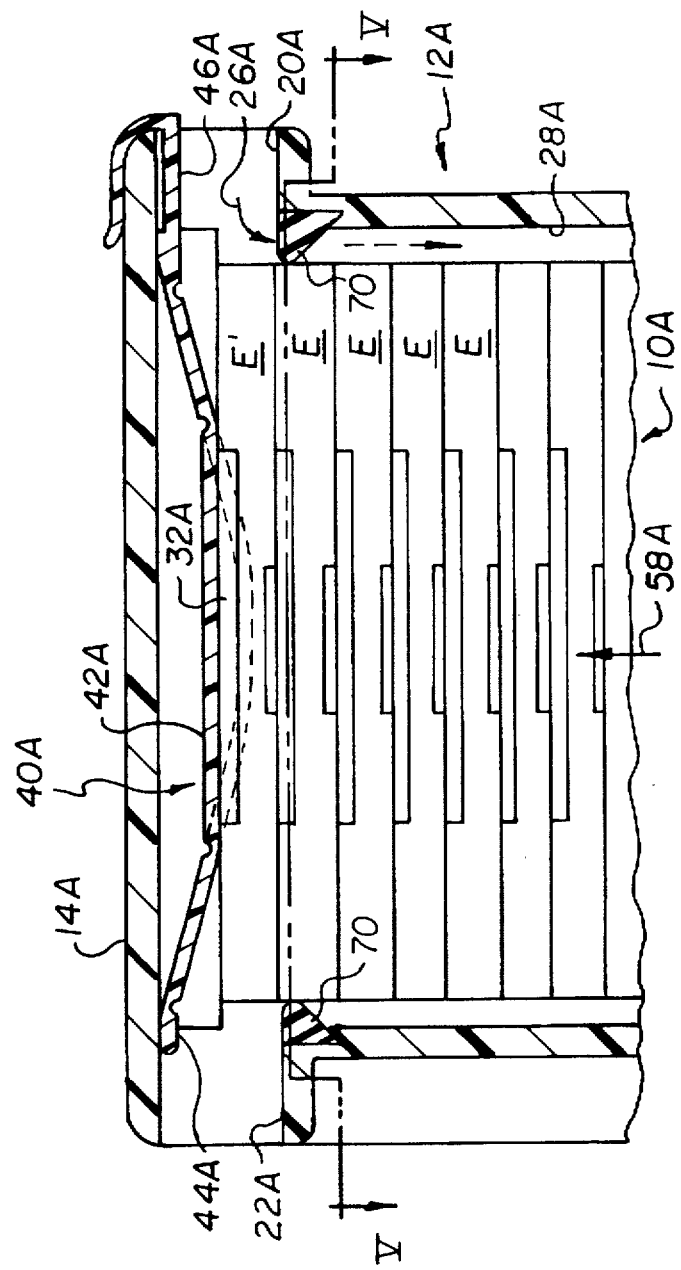
FIG. 4 is a view similar to that of FIG. 1, but illustrating an alternate embodiment.

Optionally, a seal can be provided, FIGS. 4 and 5, that protects the remaining elements E of the stack, from external air contact during storage. Parts similar to those previously described bear the same reference numeral to which the distinguishing suffix "A" is appended. Thus, stack 10A of elements E and E' are held in a cartridge 12A for dispensing them out of aperture 20A at end 14A, a cover plate 42A being in position to protect top-most element E', and biased by legs 44A and 46A, as described above. Additionally, however, a grommet 70 extends completely around the circumference of inner wall surface 28A. FIG. 5, at a position in-between apertures 20A, 22A. FIG. 4, and the opposite end from whence the force of arrow 58A is exerted. Grommet 70 seals off the entire stack of elements E against air flow that otherwise would occur along arrow 26A.

The sealing off of end 14, 14A of the cartridge is helpful, regardless of the construction of the opposite end of the cartridge (engaged by the push rod of the analyzer). However, optimum sealing of the stack of elements E occurs when said opposite end is also sealed, FIG. 6. That is, opposite end 100 of cartridge 12 is conventionally apertured at 102, without any seal. This allows a push rod 104 to enter (as shown in phantom) and push the stack upwardly, to ensure the top-most test element is constantly urged upwardly into position to be engaged by the pusher blade for ejection.

Thus, to avoid leakage at this end, and in accordance with another aspect of the invention, aperture 102 is provided with a flexible seal 110, such as a so-called "duck-bill" seal, which conventionally allows for a cylindrical object (rod 104) to penetrate temporarily (shown in phantom) and then reseal when said object is removed. The dimensions of the duck-bill are selected to accommodate the size of rod 104. The latter is preferably reduced in diameter, compared to the push rods in current use.

Figure 6:
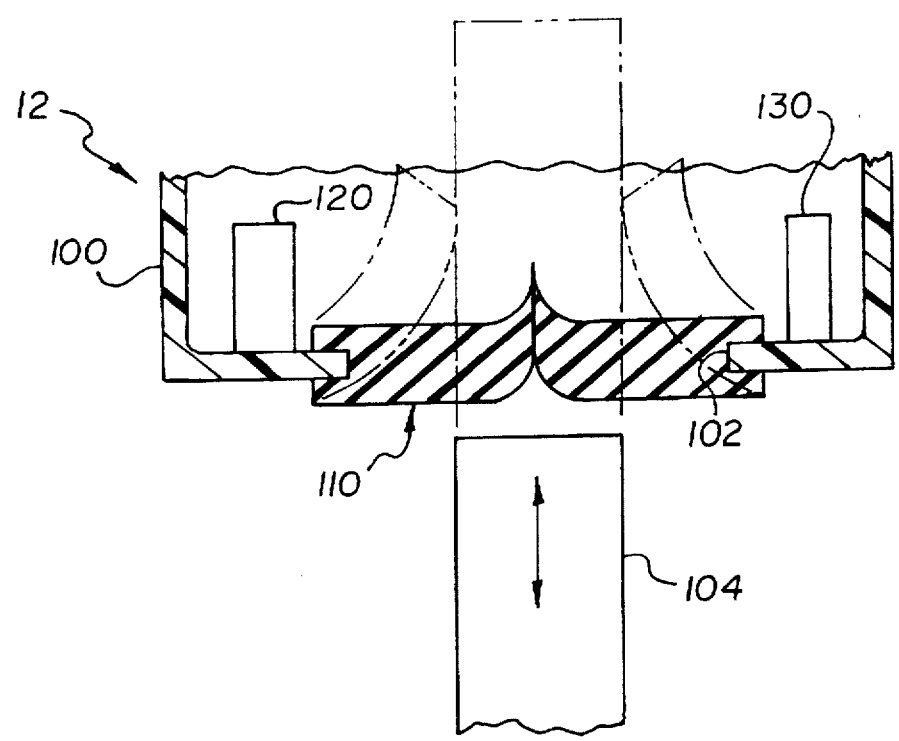
FIG. 6 is a fragmentary elevation view in section of the end of the cartridge opposite to that shown previously, illustrating how air exposure is reduced at this end as well.

Still further (not shown), any of the above-described embodiments can include, at a space below the actual stack, a desiccant or salt pad to control the relative humidity of the now-sealed stack of test elements. For example, a desiccant 120 or salt pad 130 can be mounted inside end 100. FIG. 6, or within the member 60, FIG. 1 (not shown).

It is not necessary that the cover plate for the top-most element be movable or biased away from the top end of the cartridge. Indeed, it can be part of the top end, FIG. 7. Parts similar to those previously described bear the same reference numeral to which the distinguishing suffix "B" is appended. Thus, stack 10B of elements E, E' is held in cartridge 12B having an ejection aperture 20B at top portion 14B, as described heretofore. However, instead of top-most element Et being pushed against rails 34, 36, that element is pushed up, arrow 58B, against stationary plate 42B that is integral with top portion 14B and incorporates what were the rails 34, 36 in the previous embodiments.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. In a cartridge of slide test elements stacked one upon the other and each having an opening for liquid access, said cartridge comprising:

a first dispensing end;

a second, opposing end, said first end including at least one aperture for the ejection of a slide test element closest to said first end;

the improvement wherein said cartridge further includes, adjacent to said first end and said aperture, an impervious cover plate mounted in sealing contact with said closest test element, said cover plate having a surface area that is greater in extent than the surface area of said opening;

so that said cover plate removably seals off atmospheric exposure of said opening of said closest test element;

and further including a biasing member biasing said cover plate into contact with said closest test element.

2. A cartridge as defined in claim 1, wherein said biasing member comprises a leaf spring.

3. A cartridge as defined in claim 2, wherein said leaf spring includes a leg extending from said cover plate out through said aperture.

4. A cartridge as defined in claim 3, wherein said leg is secured to said first end of said cartridge.

5. In a cartridge of slide test elements stacked one upon the other and each having an opening for liquid access, said cartridge comprising:

a first dispensing end;

a second, opposing end, said first end including at least one aperture for the ejection of a slide test element closest to said first end;

the improvement wherein said cartridge further includes, adjacent to said first end and said aperture, an impervious cover plate mounted in sealing contact with said closest test element, said cover plate having a surface area that is greater in extent than the surface area of said opening;

so that said cover plate removably seals off atmospheric exposure of said opening of said closest test element;

and further including a sealing grommet disposed completely around the inner circumference of said cartridge, located between said aperture and said opposing end, so that said grommet seals off most of said stack from atmospheric exposure via said aperture.

6. In a cartridge of slide test elements stacked one upon the other and each having an opening for liquid access, said cartridge comprising:

a first dispensing end;

a second, opposing end, said first end including at least one aperture for the ejection of a slide test element closest to said first end;

the improvement wherein said cartridge further includes, adjacent to said first end and said aperture, an impervious cover plate mounted in sealing contact with said closest test element, said cover plate having a surface area that is greater in extent than the surface area of said opening;

so that said cover plate removably seals off atmospheric exposure of said opening of said closest test element;

and further including, at said second end, an opening for access by a pusher rod, and a flexible seal in said opening capable of passing said rod through the seal and resealing said opening when said rod is removed.

7. A cartridge as defined in claim 6, and further including a desiccant or salt pad inside the cartridge for controlling the humidity of said elements.

8. A method of storing and ejecting slide test elements in a stack contained in a cartridge having an aperture at a first end of said cartridge that otherwise exposes said stack to the atmoshere and an opening at an end opposite to said first end to receive a pusher rod, each of the test elements comprising a frame having a liquid access opening allowing liquid to flow into said test element;

the method comprising the steps of releasibly covering said access opening of the test element closest to said aperture, the access openings of remaining test elements of said stack being in covered contact with a test element closer to said aperture than said remaining elements;

when a test element is needed, uncovering said access opening of said closest test element while simultaneously pushing a pusher blade into said aperture into contact with said test element closest to said aperture to eject said closest test element from said stack;

sealing off said opposite end opening of said cartridge with a flexible seal capable of passing said pusher rod through the seal and resealing said opening when said rod is removed, so that leakage of air into said cartridge through said opening is reduced, and pushing said rod through said seal when test elements are to be advanced to said first end.

* * * * *